United States Patent [19]
Stelzer

[11] Patent Number: 5,907,060
[45] Date of Patent: May 25, 1999

[54] PROCESS FOR PREPARING 3,3-DIMETHYLBUTYRIC ACID

[75] Inventor: Uwe Stelzer, Burscheid, Germany

[73] Assignee: Bayer Aktiengesellschaft, Leverkusen, Germany

[21] Appl. No.: 09/090,747

[22] Filed: Jun. 4, 1998

[30] Foreign Application Priority Data

Jun. 11, 1997 [DE] Germany .......................... 197 24 584

[51] Int. Cl.⁶ .................................................. C07C 53/00
[52] U.S. Cl. ........................................... 562/606; 562/512
[58] Field of Search ...................... 562/606, 512

[56] References Cited

U.S. PATENT DOCUMENTS

| 2,004,066 | 6/1935 | Whitmore et al. ....................... 562/606 |
| 3,892,774 | 7/1975 | Ebnother et al. . |
| 4,182,896 | 1/1980 | Teulon . |
| 5,502,229 | 3/1996 | Cho et al. . |

FOREIGN PATENT DOCUMENTS 63-222130  9/1988  Japan .

OTHER PUBLICATIONS

Stiller et al., Synthesis . . . Related Compounds, J. Med. Chem., vol. 15, No. 10, pp. 1029–1032, 1972.

Hudlicky, Reductions in Organic Chemistry, pp. 143–144, Oct. 1986.

Solomons, Organic Chemistry, fourth edition, pp. 759–760, 1988.

Stiller et al., "Synthesis and Antiinflammatory Activities . . . and Related Compounds", Journal of Medicinal Chemistry, Bd.15, Nr.10 (1972) pp. 1029–1032.

Huang–Minlon, "A Simple Modification of the Wolff–Kishner Reduction", Journal of the American Chemical Society, Bd.68 (1946) pp. 2487–2488.

*Primary Examiner*—Samuel Barts
*Assistant Examiner*—Rosalynd Keys
*Attorney, Agent, or Firm*—Sprung Kramer Schaefer & Briscoe

[57] ABSTRACT

The present invention relates to a novel process for preparing 3,3-dimethylbutyric acid by reaction of trimethylpyruvic acid with hydrazine hydrate and treatment of the resulting hydrazone with a base.

1 Claim, No Drawings

PROCESS FOR PREPARING 3,3-DIMETHYLBUTYRIC ACID

The present invention relates to a novel process for preparing 3,3-dimethylbutylic acid.

It is known that 3,3-dimethylbutyric acid is obtained by reaction of tert-butanol or tert-butyl chloride with vinylidene chloride in sulphuric acid and $BF_3$. Problems are the industrial availability of 1,1-dichloroethene and the handling of $BF_3$. Furthermore, it is known that 2-aryl-2-oxocarboxylic acids can be reduced by reaction with hydrazine hydrate and subsequent heating with bases (Wolff-Kishner reduction) to give 2-arylacetic acids (see, for example, Monath. Chem. 1952, 83, 883, J. Med. Chem. 1972, 15, 1029 and J. Heterocycl. Chem. 1990, 27, 1489).

It is an object of the present invention to provide a simple process suitable for industry for preparing 3,3-dimethylbutyric acid.

The present invention, accordingly, provides a process for preparing 3,3-dimethylbutyric acid of the formula (I)

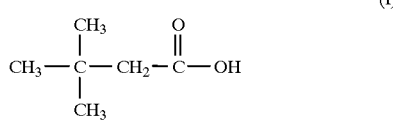

(I)

characterized in that trimethylpyruvic acid of the formula (II)

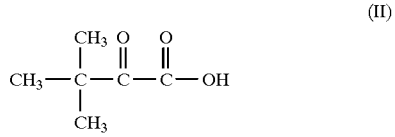

(II)

is, if appropriate in the presence of a diluent, reacted with hydrazine hydrate to give the hydrazone of the formula (III)

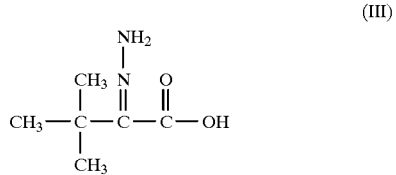

(III)

and this is subsequently, if appropriate in the presence of a diluent, treated with a base.

The process according to the invention provides 3,3-dimethylbutyric acid selectively and in high yields. This is surprising, since, according to the prior art, one would have expected tert-butylglyoxylic acid to decarboxylate very easily on heating with amine derivatives (for example aniline) to give trimethylacetaldehyde (Houben-Weyl, Methoden der organischen Chemie, Volume VII/1, page 320).

Furthermore, thermal elimination of $CO_2$ at 200 to 220° C. results in a high proportion of pivalic acid (J. Org. Chem. 35, 3726 (1970)). This is in accordance with the general statement that α-ketocarboxylic acids decarboxylate very easily (Houben-Weyl, Volume VII/1, page 317).

Using, for example, triglycol as diluent and potassium hydroxide as base, the course of the process according to the invention can be represented by the following equation:

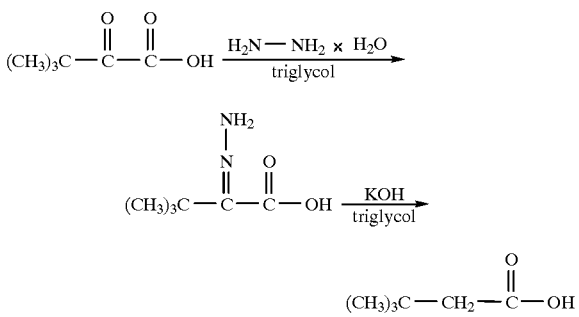

The 3,3-dimethylbutyric acid of the formula (I) prepared according to the invention is known (see, for example, J. Org. Chem. 6, 132 (1941)).

The trimethylpyruvic acid of the formula (II) used as starting material is known (see Houben-Weyl, Methoden der Organischen Chemie, Volume VII/1, page 320) and is commercially available or can be prepared in a simple manner by oxidizing pinacolone to tert-glyoxylic acid.

Also known are the hydrazone of the formula (III) (see J. Prakt. Chem. 152, 324 (1939)) and hydrazine hydrate.

Suitable diluents for the first step of the process according to the invention are the following solvents:

Alcohols, in particular polyalcohols such as diglycol and triglycol (triethylene glycol), furthermore methanol, ethanol, n- or i-propanol, n-, i-, sec- or tert-butanol, octanol, hexanol, etc., ethanediol, propane-1,2-diol, ethoxyethanol, methoxyethanol, diethylene glycol monomethyl ether, diethylene glycol monoethyl ether or sulphoxides, such as dimethyl sulphoxide; sulphones, such as sulpholane or mixtures thereof with water.

Preference is given to using triglycol and diglycol.

Suitable diluents for the second step of the process according to the invention are the following solvents:

Alcohols, in particular polyalcohols such as diglycol and triglycol (triethylene glycol), furthermore methanol, ethanol, n- or i-propanol, n-, i-, sec- or tert-butanol, octanol, hexanol, etc., ethanediol, propane-1,2-diol, ethoxyethanol, methoxyethanol, diethylene glycol monomethyl ether, diethylene glycol monoethyl ether or sulphoxides, such as dimethyl sulphoxide.

Preference is given to using diglycol and triethylene glycol.

Preferred bases for carrying out the second step of the process according to the invention are alkali metal hydroxides or alkali metal alkoxides. Examples include sodium hydroxide, potassium hydroxide, sodium methoxide and sodium ethoxide and potassium tert-butoxide.

Preference is given to using potassium hydroxide or sodium hydroxide.

The first step of the process according to the invention is carried out at temperatures between 0° C. and 200° C., preferably between 20° C. and 180° C.

The second step of the process according to the invention is carried out at temperatures between 100° C. and 280° C., preferably between 100° C. and 250° C.

Both steps are usually carried out under atmospheric pressure.

When carrying out the process according to the invention, in the first step 1 to 10 mol, preferably 1 to 7 mol, of hydrazine hydrate are employed per mole of the compound of the formula (II).

In the second step, 1 to 10 mol, preferably 1 to 7 mol, of base are employed per mole of the compound of the formula (III).

The first step of the process according to the invention is generally carried out by heating trimethylpyruvic acid together with hydrazine hydrate in a suitable diluent until the reaction has ended and, if required, removing water azeotropically.

For work-up, the alcoholic solution is evaporated to dryness under reduced pressure. The resulting hydrazone can usually be employed directly for the second step.

The second step of the process according to the invention is generally carried out by heating the compound of the formula (III) obtained by the first step together with the stated amount of base in a suitable diluent to the stated temperature until the evolution of gas (elimination of nitrogen) has ended.

For work-up, the reaction mixture is, for example, admixed with water and acidified and the product is extracted with a suitable extractant and subsequently distilled.

Examples of suitable extractants are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl butyl ether, methyl t-amyl ether, 1,2-dimethoxyethane or 1,2-diethoxyethane; nitriles, such as acetonitrile, propionitrile, n- or i-butyronitrile or benzonitrile; esters such as methyl acetate or ethyl acetate.

In a particular embodiment of the process according to the invention, the intermediate of the formula (III) is not isolated, but the first and the second steps are combined and carried out as a one-pot reaction.

This is carried out, for example, by heating the compound of the formula (II), hydrazine hydrate and the base in a suitable solvent (see above) under reflux until no more hydrazone is formed, distilling off excess hydrazine hydrate and continuing to heat the residue until the evolution of gas has ended. Subsequently, the product is worked up, for example, as described above.

3,3-Dimethylbutyric acid can be employed as an intermediate for the synthesis of insecticidally, fungicidally or herbicidally active compounds (see, for example, EP-A-0 528 156).

EXAMPLE 28 g of trimethylpyruvic acid, 30 g of hydrazine hydrate and 62.8 g of potassium hydroxide in 200 ml of triglycol (triethylene glycol) are heated at reflux temperature for 2 hours. Excess hydrazine hydrate is subsequently distilled off and heating is continued until the evolution of gas ceases. The internal temperature reaches 190 to 200° C. After cooling, the mixture is admixed with 300 ml of $H_2O$ and adjusted to pH 2 with concentrated hydrochloric acid. The aqueous phase is extracted repeatedly with toluene and the combined organic phases are subjected to fractional distillation. 22.4 g (90% of theory) of 3,3-dimethylbutyric acid are isolated at 66 to 68° C. and 8 mbar.

I claim:

1. Process for preparing 3,3-dimethylbutyric acid of the formula (I),

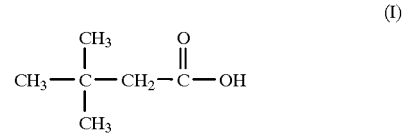

characterized in that trimethylpyruvic acid of the formula (II)

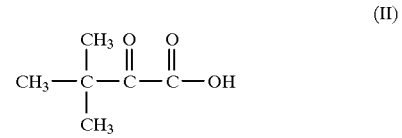

is, if appropriate in the presence of a diluent, reacted with hydrazine hydrate to give the hydrazone of the formula (III)

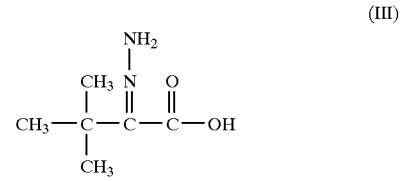

and this is subsequently, if appropriate in the presence of a diluent, treated with a base.

* * * * *